(12) United States Patent
Cross

(10) Patent No.: US 7,623,285 B2
(45) Date of Patent: Nov. 24, 2009

(54) METHOD AND DEVICE FOR OPTO-ACOUSTICAL IMAGERY

(75) Inventor: Michel Jean Cross, Villepinte (FR)

(73) Assignee: Centre National de la Recherche and Scientifique (FR)

( * ) Notice: Subject to any disclaimer, the term of this patent is extended or adjusted under 35 U.S.C. 154(b) by 167 days.

(21) Appl. No.: 10/549,511

(22) PCT Filed: Mar. 16, 2004

(86) PCT No.: PCT/FR2004/000640
§ 371 (c)(1),
(2), (4) Date: Feb. 15, 2007

(87) PCT Pub. No.: WO2004/085978
PCT Pub. Date: Oct. 7, 2004

(65) Prior Publication Data
US 2007/0151343 A1    Jul. 5, 2007

(30) Foreign Application Priority Data
Mar. 19, 2003    (FR) .................................. 03 03341

(51) Int. Cl.
*G02F 1/11* (2006.01)
(52) U.S. Cl. ........................................ 359/285; 359/287
(58) Field of Classification Search .................. 359/285
See application file for complete search history.

(56) References Cited

U.S. PATENT DOCUMENTS

| | | | | |
|---|---|---|---|---|
| 3,772,457 A | 11/1973 | Mascovski | ................... | 178/6.8 |
| 4,696,061 A * | 9/1987 | Labrum | ....................... | 398/163 |
| 5,174,298 A | 12/1992 | Dolfi et al. | ................... | 128/665 |
| 5,286,968 A | 2/1994 | Fournier et al. | .......... | 250/208.1 |
| 5,313,315 A | 5/1994 | Feinberg et al. | ................ | 359/4 |
| 5,684,588 A | 11/1997 | Khoury et al. | ............... | 356/347 |
| 6,330,086 B1 | 12/2001 | Collot et al. | .................... | 359/9 |

(Continued)

FOREIGN PATENT DOCUMENTS

FR      2 617 602      1/1989

(Continued)

OTHER PUBLICATIONS

Gross et al., "Shot-noise Detection of Ultrasound-tagged Photons in Ultrasound-modulated Optical Imaging", Optics Letters 28:2482-2484, 2003.

(Continued)

*Primary Examiner*—Jordan M. Schwartz
*Assistant Examiner*—James C Jones
(74) *Attorney, Agent, or Firm*—Fish & Richardson P.C.

(57) ABSTRACT

The inventive method for opto-acoustical imagery of an image object consists in a) generating an incident optical wave and a reference optical wave coherent therewith, b) oscillating the image object area at an acoustic frequency, c) sending the incident wave to said image object, thereby generating a diffused signal wave, d) sending at least one part of said diffused signal wave to a detection device, e) sending the reference optical wave to the detection device avoiding the image object, thereby generating an interferogram I (r, t), f) extracting digital information from said interferogram I (r, t), and in g) obtaining co-ordinates from one measurement point of the image object associated to said digital information.

29 Claims, 4 Drawing Sheets

U.S. PATENT DOCUMENTS 6,401,540 B1  6/2002  Deason et al. ............... 73/657

FOREIGN PATENT DOCUMENTS

FR  2 774 887  8/1999

OTHER PUBLICATIONS

Le Clerc et al., "Numerical Heterodyne Holography with Two-dimensional Photodetector Arrays", Optics Letters 25:716-718, 2000.

Lev et al., "Direct, Noninvasive Detection of Photon Density in Turbid Media", Optics Letters 27:473-475, 2002.

Lev et al., "Ultrasound Tagged Light Imaging in Turbid Media in a Reflectance Geometry", Optics Letters 25:378-380, 2000.

Leveque et al., "Ultrasonic Tagging of Photon Paths in Scattering Media: Parallel Speckle Modulation Processing", 24:181-183, 1999.

Leveque-Fort, "Three-dimensional Acousto-optic Imaging in Biological Tissues with Parallel Signal Processing", Applied Optics 40:1029-1036, 2000.

Li et al., "Methods for Parallel-Detection-Based Ultrasound-Modulated Optical Tomography", Applied Optics 41:2079-2084, 2002.

Wang, "Mechanisms of Ultrasonic Modulation of Multiply Scattered Coherent Light: A Monte Carlo Model", Optics Letters 26:1191-1193, 2001.

Wang et al., "Sonoluminescent Tomography of Strongly Scattering Media", Optics Letters 23:561-563, 1998.

Yao et al., "Frequency-Swept Ultrasound-Modulated Optical Tomography in Biological Tissue by Use of Parallel Detection", Optics Letters 25:734-736, 2000.

Yao et al., "Theoretical and Experimental Studies of Ultrasound-Modulated Optical Tomography in Biological Tissue", Applied Optics 39:659-664, 2000.

Zhu et al., "Imager that Combines Near-Infrared Diffusive Light and Ultrasound", Optics Letters 34:1050-1052, 1999.

\* cited by examiner

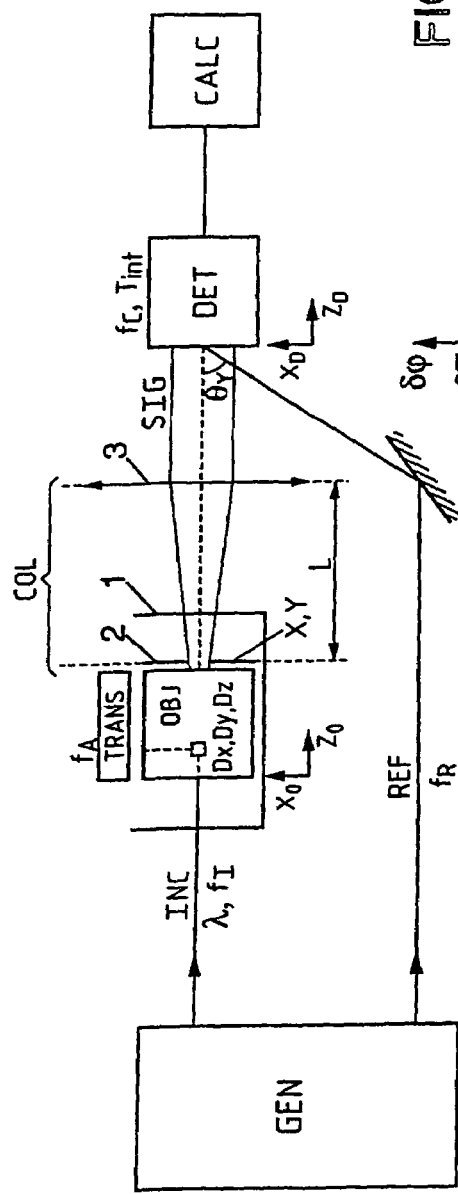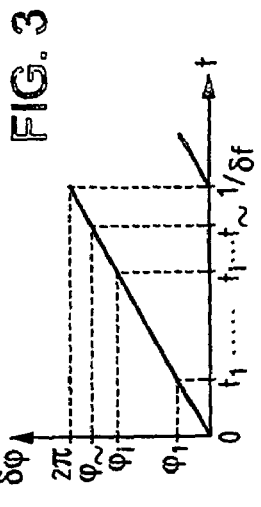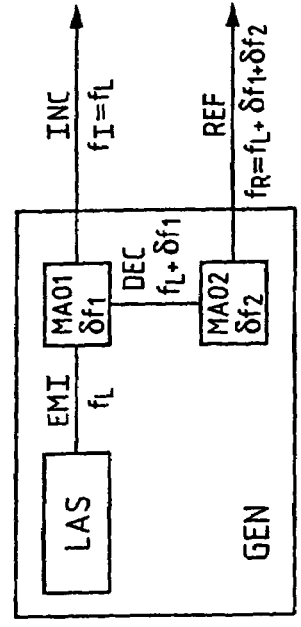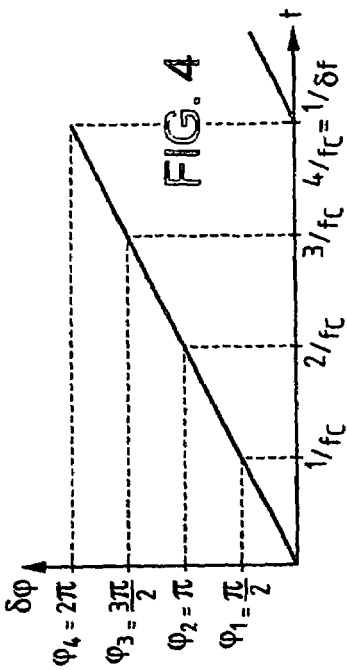

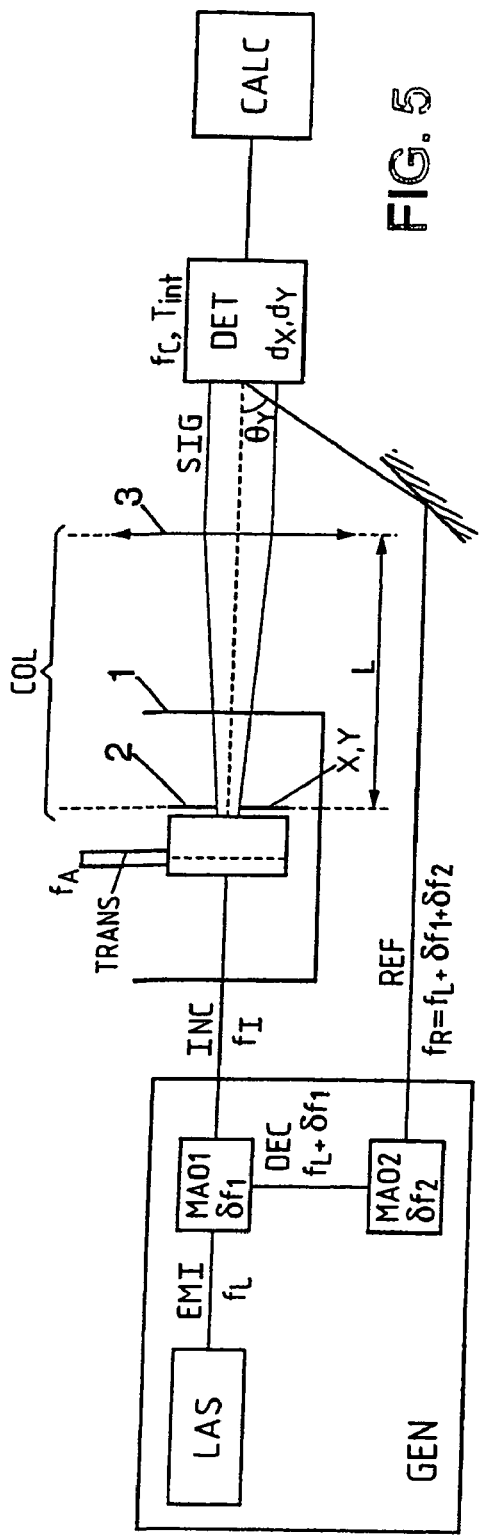
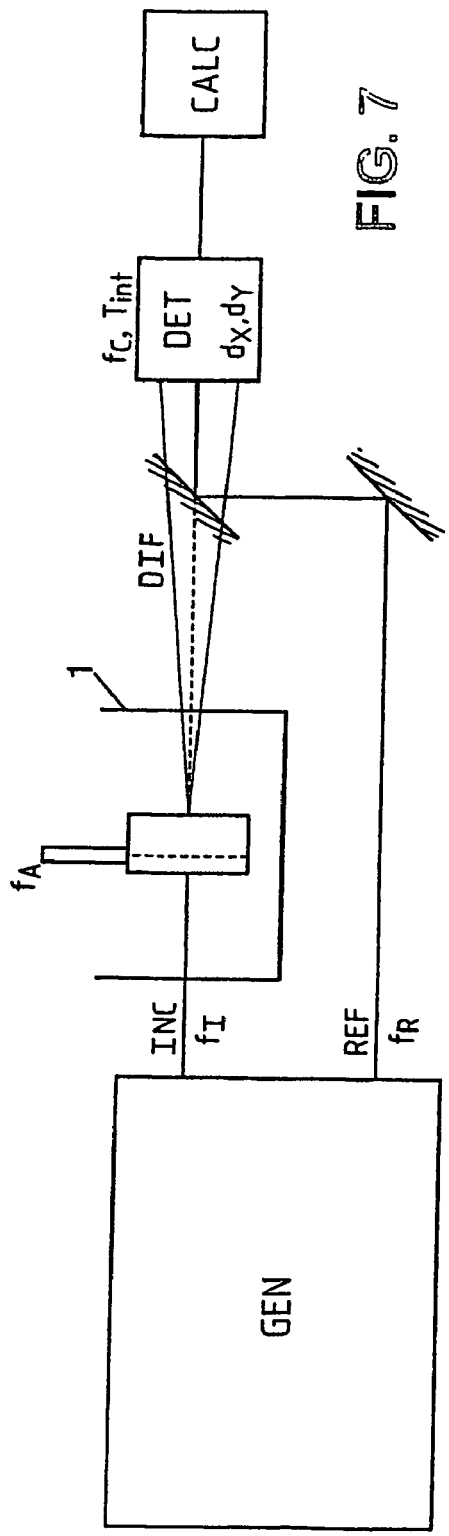
FIG. 5
FIG. 7

METHOD AND DEVICE FOR OPTO-ACOUSTICAL IMAGERY

FIELD OF THE INVENTION

The present invention relates to a method and installation for acousto-optical imaging.

BACKGROUND OF THE INVENTION

In acousto-optical imaging, one detects the beat of a local oscillator with an acoustic component of a signal wave scattered by an object to be imaged, shifted in frequency by the vibration at an acoustic frequency of a point of said object to be imaged from which one seeks to obtain information of an optical nature.

In monopixel acousto-optical imaging, the measurement of the beat between the component of the signal wave scattered without frequency shift, which serves as local oscillator, and the acoustic component of the signal wave, which carries the information, exhibits significant noise since the measurement of said beat is performed at just one point of the detection plane whereas each of these two components varies in a random manner in this plane. It is necessary to perform a summation over time of the square of the amplitude of said beat to obtain information exhibiting a better signal/noise ratio.

To alleviate this drawback, it is possible to use a multipixel detection device, by performing a summation over the pixels of the detection device, rather than in time, such as described in "Ultrasonic tagging of photon paths in scattering media: parallel speckle modulation processing", Optics Letters, Vol. 24, No. 3, 1st Feb. 1999, page 181. In this context, it is necessary to modulate the power of the laser at a frequency close to the acoustic frequency, so that the beat between the acoustic component of the signal wave, carrying the information, and the modulation lateral band (the local oscillator) is of sufficiently low frequency to be detected by a multipixel detection device, which in general possesses a low acquisition frequency. Nevertheless, a major problem remains, in that the weight of the local oscillator is in general too low. The heterodyne gain is then too low to be able to perform heterodyne detection with optimal noise.

The present invention is aimed in particular at alleviating these drawbacks.

SUMMARY OF THE INVENTION

For this purpose, there is provided according to the invention, a method of acousto-optical imaging of an object to be imaged comprising the steps consisting in:
(a) generating an incident optical wave, of frequency $f_I$, and a reference optical wave, of frequency $f_R$, this reference wave being coherent with the incident wave, and exhibiting therewith a known phase difference $\phi_i(t)$,
(b) vibrating in a first object direction and at an acoustic frequency $f_A$, a zone of the object to be imaged with the aid of a vibration generating device,
(c) applying said incident wave to the object to be imaged, and thus generating a scattered signal wave,
(d) applying at least a part of the scattered signal wave to a detection device,
(e) applying the reference wave to the detection device without making it pass through the object to be imaged, thereby generating at the point r of the detection device an interferogram $I(r, t)$ varying over time t,
(f) extracting a digital information item from the interferogram $I(r, t)$, and
(g) obtaining the coordinates of a point of measurement of the object to be imaged, to which the digital information item relates.

Thus the reference wave, which serves as local oscillator, need not pass through the object to be imaged. This makes it possible to have a sufficient level of local oscillator, and to extract, with a better signal/noise ratio, useful information relating to the point of measurement for example for imaging purposes, in particular medical imaging. Moreover, this imaging method makes it possible to obtain a utilizable signal even with low acoustic or optical powers, that are for example compatible with the safety standards for imaged tissues associated with medical imaging.

In preferred embodiments of the invention, recourse may furthermore possibly be had to one and/or other of the following provisions:

in the course of step (f), an acoustic component of the part of the scattered signal wave applied to the detection device is detected, this acoustic component being at a frequency corresponding to the sum of the frequency $f_I$ of the incident wave and of a harmonic of the acoustic frequency $f_A$ ($f_I \pm H.f_A$, H nonzero integer);

in the course of step (a), said reference wave is generated at a frequency $f_R$ equal or substantially equal to the sum of the frequency $f_I$ of the incident wave and of said harmonic of the acoustic frequency $f_A$ ($f_R \approx f_I \pm H.f_A$, H nonzero integer);

in the course of step (b), an acoustic wave is generated, focused at a focal point situated in the object to be imaged, and in the course of step (g), the coordinates of the measurement point are obtained as being the coordinates of said focal point;

steps (a) to (g) are repeated for various focal points of the acoustic wave in the object to be imaged, these various focal points being aligned along the first object direction;

in the course of a first iteration, steps (a) to (f) are performed for a first frequency $f_A$ of the acoustic wave and a first frequency $f_R$ of the reference wave, in the course of at least a second iteration, steps (a) to (f) are repeated for a second frequency $f'_A$ of the acoustic wave and a second frequency $f'_R$ of the reference wave, these second frequencies being coded respectively with the first frequencies, the method furthermore comprising a step in the course of which:

(f') at least one digital information item is obtained by decoding said digital information items obtained in the course of steps (f) of each iteration as a function of the frequencies used, and, in the course of step (g), the coordinates of at least one point of measurement of the object to be imaged to which the digital information item obtained in the course of step (f') relates are obtained, by decoding said digital information items obtained in the course of steps (f) of each iteration as a function of the frequencies used;

the sequence of following operations is performed:
a scan is performed of the frequency of the acoustic wave, which is focused on an interval of points with coordinates ([U−Dx, U+Dx], V, W) extending around the point with coordinates (U, V, W) along the first object direction,
a scan is performed jointly of the frequency $f_R$ of the reference wave in such a way as to keep $f_R$ substantially equal or equal to $f_I \pm H.f_A$, H being a nonzero integer, an interferogram $I(f_A, V, W, r)$ associated with the set of points $([U-Dx, U+Dx], V, W)$ of the extended interval is recorded for each pixel r and for each frequency $f_A$;

a 1D frequency→time Fourier transformation is performed, for each pixel r, according to the frequency $f_A$ of the interferogram $I(f_A, V, W, r)$, and at least one interferogram $I(r)$ associated at least with a measurement point with coordinates $(U', V, W)$ is obtained by replacing the time obtained after the Fourier transform with the magnitude $U'$ along the first object direction with the aid of the speed of propagation of the acoustic wave in the object to be imaged ($U'$ possibly equalling U);

at least steps (a) to (g) are repeated after having imposed a displacement of the vibration generating device relative to the object to be imaged along a direction not parallel to the first object direction of the object to be imaged;

in the course of step (f), the complex amplitude $E_s(r)$ of the acoustic component is estimated on the basis of the interferogram $I(r, t)$;

the detection device used is a monopixel detector, and, in the course of step (f), the digital information item is obtained as being the intensity of the field of complex amplitude $E_s(r)$ scattered by the object;

the detection device used is a multipixel detector, and in the course of step (f), the digital information is extracted as being the sum over at least a part of the pixels r of the detection device of the intensity of the complex amplitude field $E_s(r)$ scattered by the object;

in the course of step (d) a spatial filtering device is used, in such a way as to limit, along at least one direction, the angular extent of the part of the scattered signal wave which is seen by each pixel of the detection device (it is thus possible to define a mean angular direction for the part of the scattered signal wave which is seen by each pixel of the detection device);

a spatial filtering device comprising a diaphragm, of dimensions X along a first diaphragm direction and Y along a third diaphragm direction, and a lens of focal length L with object focus situated directly downstream of the object to be imaged is used so as to limit the angular extent of the part of the scattered signal wave which is seen by each pixel of the detection device, and the reference wave applied to the detection device is globally a plane wave (the direction of application of the acoustic wave, of the incident wave, and the directions of the diaphragm are not necessarily linked);

a spatial filtering device comprising a diaphragm of dimensions X along the first diaphragm direction and Y along the third diaphragm direction, disposed between the object to be imaged and the detection device at a distance L from the latter is used, so as to limit the angular extent of the part of the scattered signal wave which is seen by each pixel of the detection device, and the reference wave applied to the detection device is a spherical wave emanating from a source point situated in the plane of the diaphragm (the direction of application of the acoustic wave, of the incident wave, and the directions for the diaphragm are not necessarily linked);

the reference wave and the scattered signal wave interfere on the detection device while forming a nonzero angle $\theta_Y$, $\theta_Y$ being measured in the plane of incidence of these two waves on the detection device;

the detection device used is a multipixel detector, and the part of the acoustic component, of complex amplitude $E_s(r)$, which varies rapidly in space in the plane of the detection device is isolated (the detection device is in a plane quasi-orthogonal to the direction of the reference wave, and the part that one seeks to isolate corresponds to the components of the interferogram $I(r)$, which vary rapidly in space and slowly in time)

the detection device comprises pixels disposed as a matrix comprising rows along a first detector direction and columns along a third detector direction, and step (f) comprises the following steps:

(f1) for at least one row or column a 1D Fourier transform is done along this row or column of the detection device to the space of wave vectors, of the complex amplitude $E_s(r)$, and a field $TF_1 E_s(k)$, is thus obtained for this row or column, (f2) several zones of summation are defined in the space of wave vectors, (f3) the intensities of the field $TF_1 E_s(k)$ at each point k of at least one zone are summed in this zone, and (f4) the digital information item is extracted as being a linear combination of the sums thus obtained at each zone (this linear combination possibly comprising just one term);

the detection device comprises pixels disposed in a matrix comprising rows along a first detector direction and columns along a third detector direction, and step (f) comprises the following steps:

(f1) a 2D Fourier transform is done of the complex amplitude $E_s(r)$, from the plain of the detection device to the space of wave vectors, and a field $TF_2 E_s(k)$, is thus obtained, (f2) several zones of summation are defined in the space of wave vectors, (f3) the intensities of the field $TF_2 E_s(k)$ at each point k of at least one zone are summed in this zone, and (f4) the digital information item is extracted as being a linear combination of the sums thus obtained at each zone (this linear combination possibly comprising just one term);

the angle $\theta_Y$ is about equal to $3Y/2L$, in the course of step (f2) are defined a first zone of summation, the so-called central zone, a second zone of summation, the so-called left zone, and a third zone of summation the so-called right zone, and, in the course of step (f4), the digital information item is extracted as being a linear combination of the value of the sum of the left zone and of the sum of the right zone (this linear combination possibly comprising just one term);

in the course of step (a),
a laser source of wavelength λ emits an emission wave, of frequency $f_L$,
amplitude modulation means of the emission wave generate a carrier wave of incident frequency $f_I$, and at least one amplitude modulation lateral band, which corresponds to a wave of frequency $f_R$,
a semireflecting mirror, transmits a part of the lateral band wave and a part of the carrier wave forming the incident wave, and reflects a part of the carrier wave and a part of the lateral band wave forming the reference wave;

in the course of step (a),
a laser source of wavelength λ emits an emission wave, of frequency $f_L$,
a first acousto-optical modulator transmits a part of the emission wave to form the incident wave on the object to be imaged, and moreover generates a first frequency shifted wave, the frequency of which is shifted by a value $\delta f_1$, possibly negative, with respect to the emission wave, and a second acousto-optical modulator intercepts the first frequency shifted wave and generates a second frequency shifted wave, the frequency of which is shifted by a value $\delta f_2$, possibly negative, with respect to the shifted wave, the second frequency shifted wave forming the reference wave, the frequency of which is thus shifted in frequency with respect to the incident wave by a value $\delta f = \delta f_1 + \delta f_2$, thus determining a known phase difference $\phi_i(t)$ between these two waves; (usually $\delta f_1$ and $\delta f_2$ are of opposite sign);

in the course of step (a), two independent laser sources, locked in phase by electronic slaving, generate the incident and reference waves, exhibiting a known phase difference $\phi_i(t)$ between them;

in the course of step (a), a laser source of wavelength $\lambda$ emits an emission wave, of frequency $f_L$, a semireflecting mirror transmits a part of the emission wave to form the incident wave on the object to be imaged, and transmits a second part of the emission wave, a first acousto-optical modulator intercepts the second part of the emission wave and generates a first frequency shifted wave, with frequency shifted by a value $\delta f_1$, possibly negative, with respect to the emission wave, and a second acousto-optical modulator intercepts the first frequency shifted wave and generates a second frequency shifted wave, the frequency of which is shifted by a value $\delta f_2$, possibly negative, with respect to the shifted wave, the second frequency shifted wave forming the reference wave, the frequency of which is thus shifted in frequency with respect to the incident wave by a value $\delta f = \delta f_1 + \delta f_2$, thus determining a known phase difference $\phi_i(t)$ between these two waves (usually $\delta f_1$ and $\delta f_2$ are of opposite sign);

the object to be imaged is a biological tissue;

the vibration generating device is used to obtain an acoustic cue of the zone of the object to be imaged, and the digital information item extracted in step (f) is used jointly with said acoustic cue.

According to another aspect, the invention relates to an installation for acousto-optical imaging of an object to be imaged (OBJ) comprising:

means for generating an incident optical wave, of frequency $f_I$, and a reference optical wave of frequency $f_R$, this reference wave being coherent with the incident wave and exhibiting therewith a known phase difference $\phi_i(t)$, a vibration generating device for vibrating in a first object direction and at an acoustic frequency $f_A$ a zone of the object to be imaged, means for applying said incident wave to the object to be imaged, thus generating a scattered signal wave, a detection device, means for applying at least part of this scattered signal wave to the detection device, means for applying the reference wave to the detection device without making it pass through the object to be imaged, thereby generating at point r of the detection device an interferogram $I(r, t)$ varying over time t, and means for extracting a digital information item and the coordinates of a point of measurement of the object to be imaged, to which the digital information item relates, from the interferogram.

In preferred embodiments of the invention, recourse may furthermore possibly be had to one and/or other of the following provisions:

the installation furthermore comprises the following elements:

means for visualizing said digital information item relating to said point of measurement of the object to be imaged, and means for displacing the object to be imaged;

the installation furthermore comprises a spatial filtering device situated downstream of the object to be imaged.

Other aspects, aims and advantages of the invention will become apparent on reading the description of several of its embodiments given by way of nonlimiting examples.

BRIEF DESCRIPTION OF THE DRAWING

The invention will also be better understood with the aid of the drawings, in which:

FIG. 1 describes a first exemplary implementation of the method according to the present invention, FIG. 2 is a detailed diagram of an example of the device for generating two coherent waves according to the present invention, FIGS. 3 and 4 are graphs representing the phase difference between two coherent waves as a function of time, in a general manner and in a particular case, FIG. 5 describes the first exemplary implementation of the method according to the present invention with the generating device of FIG. 2, FIG. 7 represents a second exemplary implementation of the method according to the present invention.

DETAILED DESCRIPTION OF THE INVENTION

Figure 6:
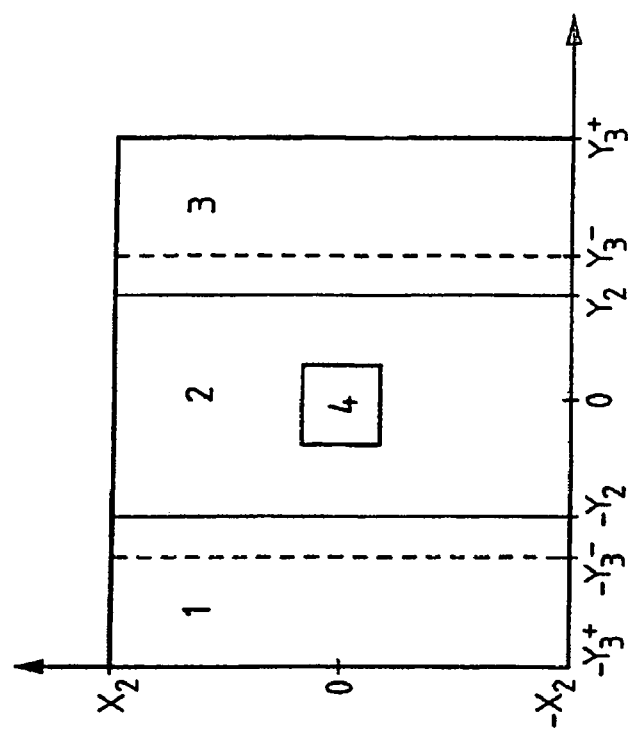
FIG. 6 represents a mapping of the signal obtained.

FIG. 1 shows a device for generating waves GEN, which generates:

an incident optical wave INC, of wavelength $\lambda$, of frequency $f_I$, applied to an object to be imaged OBJ, and a reference optical wave REF of frequency $f_R$.

The incident wave INC and reference wave REF are mutually coherent and exhibit a known phase difference $\phi_i(t)$. These optical waves may be emitted in the visible region, or possibly in the infrared or ultraviolet.

The generating device GEN is adjusted in such a way that the reference wave REF is shifted in frequency with respect to the incident wave by a value equal to $\delta f$.

There exist numerous possibilities for embodying such a generating device, and it is for example possible to use a generating device such as represented in FIG. 2. This generating device comprises:

a laser source LAS emitting an optical emission wave EMI at the frequency $f_L$, a first acousto-optical modulator MAO1 transmitting a part of the emission wave EMI to form the incident wave INC at the frequency $f_I$, and furthermore generating a wave DEC shifted by $\delta f_1$ in frequency, and a second acousto-optical modulator MAO2 intercepting the frequency shifted wave DEC, of frequency $f_L + \delta f_1$, so as to again shift this wave by a frequency $\delta f_2$ to thus generate a reference wave REF at the frequency $f_R = f_L + \delta f_1 + \delta f_2$, $\delta f_1$ and/or $\delta f_2$ possibly being negative ($\delta f_1$ and $\delta f_2$ are usually of opposite sign).

These acousto-optical modulators MAO1 and MAO2 are for example constituted by an acousto-optical cell of tellurium dioxide ($TeO_2$), oriented along a given angle relative to the wave applied thereto, namely the emission wave EMI and the shifted wave DEC respectively, and vibrating under the action of a high-frequency generator, of frequency $\delta f_1$ and $\delta f_2$ respectively, and transmit both a nondiffracted beam and a frequency shifted diffracted beam. The two acousto-optical modulators MAO1 and MAO2 performing the frequency shift of the reference wave REF with respect to the laser wave have for example frequencies of around 80 MHz, so that these two waves may be mutually shifted by a frequency shift $\delta f = \delta f_1 + \delta f_2$, which may be fixed between a few hertz and about a few tens of megahertz.

As a variant, it is also possible to use another generating device (not represented) where the incident wave INC is extracted from the laser source LAS with the aid of a semi-transparent mirror (or any other device) placed upstream of the first acousto-optical modulator MAO1, which then generates the shifted wave DEC on the basis of the part of the incident wave transmitted by the semitransparent mirror (or any other similar device placed between the laser source LAS and the first acousto-optical modulator).

It may also be possible to use two independent laser sources, locked in phase by electronic slaving, and generating incident INC and reference REF waves exhibiting a known phase difference $\phi_i(t)$ between them.

In these embodiments of a generating device, the laser source or sources LAS may for example comprise a laser diode stabilized by an external cavity with grating, emitting a laser wave EMI of wavelength $\lambda = 850$ nm and delivering a maximum power of 20 mW for a current of 65 mA. It may be possible to use a power of said laser of about 15 mW, thus giving in this example, taking account of the optical losses, a power of about 7 mW of the incident wave INC on the object to be imaged OBJ.

The two waves thus obtained, the incident wave INC at the frequency $f_I$ and the reference wave REF at the frequency $f_R$, are thus two coherent waves shifted in frequency by a value $\delta f = \delta f_1 + \delta f_2$. It is thus possible to control the phase difference $\phi_i(t)$ between these two waves.

FIG. 5 represents the first embodiment of the invention with the generating device GEN of FIG. 2.

The object to be imaged OBJ to which is applied the incident wave INC is a scattering object in respect of the optical waves, for example a sample of biological tissue. In the example considered, this sample may for example exhibit a thickness of about 20 mm in the direction of propagation of the incident wave INC.

This sample may in particular be compressed between a front plate and a downstream plate, which are perpendicular to the direction of propagation of the incident wave INC, these two plates forming part of a sample holder (not represented).

The upstream plate is for example entirely transparent and made in particular of PMMA (Plexiglas®), while the downstream plate may for example be opaque and made in particular of black Bakelite. This rear plate is pierced for example with a circular hole of diameter of about X=20 mm.

An acoustic coupling is effected between the object to be imaged OBJ and a vibration generating device TRANS situated outside the object. For this purpose, the object to be imaged OBJ and its sample holder may be installed at the center of a tank 1, for example 180 mm in diameter and 150 mm high. This tank may be furnished with plane glass windows 60 mm in diameter, 240 mm apart, and may possibly be filled with liquid serving to accomplish the acoustic coupling between the object to be imaged OBJ and the vibration generating device TRANS.

If the object to be imaged OBJ may not be immersed, or for any other reason, other means, known to the person skilled in the art, may be used to guarantee the acoustic coupling. It is for example possible to mount the vibration generating device directly on the object to be imaged OBJ.

The vibration generating device TRANS may be a transducer PZT possessing a frequency of acoustic vibration $f_A = 2.2$ MHz, and a variable focal length fixed for example at 75 mm. It is excited for example by a sinusoidal signal produced at a maximum power of 22 dBm on 50$\Omega$, i.e. 6.3 Vcc, benign in respect of biological tissues. It may be possible to use a different maximum power, for example of the order of 34 dBm or the like.

This vibration generating device is oriented along a first direction of the object $x_o$, and emits an acoustic wave of frequency $f_A$ along this first direction of the object $x_o$. A zone (Dx, Dy, Dz) of the object to be imaged, centered on a point with coordinates (U, V, W) for which one seeks to obtain information is thus made to vibrate at the frequency $f_A$ by the vibration generating device TRANS. The extent (Dy, Dz) of the vibrating object zone corresponds roughly to the dimension of the focal zone of the acoustic wave, along the transverse directions y and z, that is to say in the plane normal to the direction of propagation $x_o$ of the acoustic wave emitted by the transducer. In this plane, the focal zone is centered at (V, W). U corresponds to the distance between the acoustic transducer and the focal point of the latter along the direction of propagation of the acoustic wave. Around this focal point, a certain zone, of variable extent Dx depending on the type of transducer used and the nature of the object to be imaged, among other things, vibrates at the acoustic frequency $f_A$. Thus, the position and the orientation of the transducer and the position of its focal point determine a point of measurement of the object to be imaged OBJ, with coordinates (U, V, W).

The incident wave INC is applied to the object to be imaged OBJ, along a second object direction $z_o$, possibly identical to the first object direction $x_o$, to form a scattered signal wave DIF which is scattered by the object in all directions. Inside the object to be imaged OBJ, a part of the wave passes through the zone (Dx, Dy, Dz) of the object to be imaged OBJ vibrating at the acoustic frequency $f_A$. The movement of the points of the object that are likely to scatter generates a modulation of the phase of the scattered wave at the acoustic frequency $f_A$. The vibration furthermore produces a modulation of the optical index of the medium (also at the frequency $f_A$). These two effects give rise to the generation of an acoustic lateral band shifted in frequency by $f_A$ vis-à-vis the incident wave of frequency $f_I$ which passes through the medium. The scattered signal wave DIF therefore possesses a frequency shifted acoustic component of frequency $f_{OA} = f_I \pm H \cdot f_A$ (where H=1, 2, ... is the harmonic rank, in general H=1). The principle of acousto-optical imaging then consists in detecting on a detection device DET this acoustic component of the signal wave scattered by the object, by making this acoustic component of the scattered signal wave interfere with a local oscillator of approximately similar frequency. This is performed according to the invention by using the reference wave REF not passing through the object to be imaged OBJ, as local oscillator for the detection device.

The detection device exhibits at least one detection cell in a plane $x_D$, $y_D$ almost normal to the direction of observation $z_D$ (in the illustrative examples given in the figures, $x_D$, $y_D$, $z_D$ correspond to $x_o$, $y_o$, $z_o$).

It is possible to use a multipixel detection device DET, for example a digital CCD camera (12 bits) consisting of 1280×1024 square pixels of size $d_x=d_y=6.7$ μm. The CCD camera is chosen to have a sufficient quantum yield for a wave at 850 nm, for example 5% or more. The camera may be of the "full frame" type (non interlaced) or frame transfer type, with a detection frequency of for example $f_c=12.5$ Hz.

A device is used to make the scattered signal wave DIF emanating from the object to be imaged OBJ interfere on the detection device DET with the reference wave REF. To perform effective detection on pixels of finite dimension it is necessary for these two waves to be almost colinear (forming an angle of 5° at most). It is possible for example to use a semireflecting pane or a beam splitter prism to guide the reference wave REF toward the detection device DET.

We shall see that it may be useful to shift the direction of the reference wave REF angularly from the mean direction of the scattered signal wave DIF, by an angle $\theta_Y$. For the following description and in FIGS. 1, 5, 7 and 9, the angular shift is performed along the direction y, the direction of the acoustic wave is x, the direction of observation is the same as that of the incident wave INC (direction z) and the matrix of the CCD detector is oriented along x and y, but these orientations are defined only by way of example.

The scattered signal wave DIF and the reference wave REF are made to interfere on the detection device, and with the aid of the latter an interferogram I(U, V, W, r, t), is recorded, taken at the instant t, at the point r of the detection device, and which corresponds to the point of measurement with coordinates (U, V, W) of the object to be imaged, vibrating at the acoustic frequency $f_A$.

This installation may be coupled with a processing device CALC, capable of extracting from the time interferogram recorded a digital information item relating to the measurement point, with coordinates (U, V, W), this information item subsequently being displayable in an image of the object. This processing involves the calculation of the complex amplitude $E_s$(U, V, W, r) of the acoustic component of the scattered field, frequency shifted by the acoustic vibration, on the detector.

In a first nonlimiting embodiment of the determination of the complex amplitude $E_s$(U, V, W, r), the acoustic wave, of fixed frequency $f_A$, is focused at the measurement point with coordinates (U, V, W), and the frequency $f_R$ of the reference wave REF is chosen in such a way as to perform a N-phase demodulation, in particular a 4-phase demodulation (N=4), as explained hereinbelow.

The measurement point, with coordinates (U, V, W), of the object to be imaged OBJ vibrating at the acoustic frequency $f_A$, the scattered signal wave DIF contains an acoustic component of frequency $f_I+f_A$. The processing unit CALC processes the interferogram I(U, V, W, r, t) which can vary over time by a four-phase demodulation in the following manner. The frequency shift δf is firstly chosen between the incident wave INC and the reference wave REF such that $\delta f = f_A + f_C/4 = f_A + 3.125$ Hz. The detection could however also be performed for any number N at least equal to 2 of phases, and the frequency of the reference wave adapted by taking $\delta f = f_A + f_C/N$.

One then measures N interferograms, each during a time $T_{int}$, each interferogram corresponding to a known distinct phase difference $\phi_i$ between the incident wave INC and the reference wave REF. The reference wave being at the frequency $f_R = f_I + f_A + f_C/N$, and the acoustic component of the signal wave being at the frequency $f_I + f_A$, the phase difference between the reference wave REF and the acoustic component of the signal wave is, as represented in FIG. 3 in a general manner and in FIG. 4 for N equal 4, linear per interval as a function of time and goes from 0 to 2Π over a time interval equal to $N/f_C$.

We thus detect N interferograms $I_1^1$(U, V, W, r, t), ..., $I_N^1$(U, V, W, r, t), ..., $I_N^1$(U, V, W, r, t) corresponding to N distinct values $\phi_i$ of the phase difference, N being at least equal to 2, and in the case of FIG. 4 being equal to 4.

This operation may be performed a number n at least equal to 1 of times, and for example for n=3, so as to obtain, for each known phase difference $\phi_i$, n interferograms $I_i^k$(U, V, W, r, t) (i=1 ... N, k=1 ... n).

For 12 interferograms, i.e. 3 cycles of 4 phases (N=4, n=3), the total duration of the measurement is for example of the order of a second.

The 4-phase demodulation calculation may be performed separately for each of the pixels r of the detection device. The processing device CALC carries out in fact for each pixel r of the detection device, the following operations:

the integration of the intensity measured by the detector over the duration of a frame of the CCD camera (1/12.5 s): $I_i^k$(U, V, W, r)=$(1/T_{int})\int I$(U, V, W, r, t) dt taken between instants $t=t_{ik}$ and $t=t_{ik}+T_{int}$.

for each given phase $\phi_i$, averaging of the n interferograms $I_i^k$(U, V, W, r) (with k=1 ... n) detected for this phase to obtain N averaged interferograms $I_i$(U, V, W, r).

a demodulation with N phases of the N interferograms measured so as to obtain the information regarding the complex amplitude $E_s$(U, V, W, r) of the acoustic component of the signal wave DIF scattered by the object. For example, for n equal to 1, and in the particular case of FIG. 4 where N is equal to 4 and where $\phi_1=\Pi/2$, $\phi_2=\Pi$, $\phi_3=3\Pi/2$, $\phi_4=2\Pi$, the complex amplitude $E_s$(U, V, W, r) of the acoustic component is proportional to $(I_4-I_2)+j(I_1-I_3)$ (where j is the complex number such that $j^2=-1$), and the intensity associated with the object to be imaged OBJ also, since the reference wave is considered to exhibit a constant complex amplitude in space and in time.

To determine the complex amplitude $E_s$(U, V, W, r) of the acoustic component of the scattered signal wave DIF, a certain number of other techniques are commonly employed, known to the person skilled in the art.

A second mode of determination of the complex amplitude $E_s$(U, V, W, r) of the acoustic component consists for example in using the so-called "frequency chirping" proceeding. In this case, instead of focusing at the magnitude U along the direction x an acoustic wave of fixed frequency $f_A$, it is possible to perform the sequence of following operations:

a scan is performed of the frequency $f_A$ of the acoustic wave, which is focused on an interval of [U−Dx, U+Dx] extending around U;

a scan is performed jointly with the first scan, of the frequency $f_R$ of the reference wave in such a way as to keep the condition $f_R=f_I\pm H.f_A$, (where H is the harmonic rank, in general 1) (it will be noted that here the reference wave has the same frequency as the acoustic component that one seeks to detect);

the interferogram $I(f_A, V, W, r)$ associated with the set of points ([U−Dx, U+Dx], V, W) of the extended interval is recorded for each pixel with location r and for each frequency $f_A$;

a 1D frequency→time Fourier transformation is performed, for each pixel with location r, according to the frequency $f_A$ of the interferogram $I(f_A, V, W, r)$, and the complex interferograms $I(U, V, W, r)$ associated with the various values of the magnitude U along the direction x are obtained by replacing the time obtained after the Fourier transform with the magnitude U along x with the aid of the speed of propagation of the acoustic wave in the object to be imaged.

The reference wave being approximately a plane wave of constant amplitude, the complex interferogram $I(U, V, W, r)$ thus decoded is directly proportional to the complex amplitude $E_s(U, V, W, r)$ of the acoustic component of the scattered signal wave DIF that one seeks to determine.

There exist numerous variants of the "frequency chirping" technique which consist in replacing the coding along the x direction with a frequency coding according to $f_A$ and $f_R$. These techniques, or others, may equally well be used to determine $E_s(U, V, W, r)$ in the context of this invention.

Provision may furthermore be made in this first embodiment for a spatial filtering device COL (FIGS. 1 and 5), which makes it possible to limit the angular extent of the part of the signal wave seen by each pixel of the detection device. We shall see that this device is useful for controlling the speckle grain dimension associated with the scattered signal wave DIF, in the plane of the detection device.

To perform the detection it may be beneficial to make sure that the dimension of the speckle grains is adapted to the size of the pixels of the camera. This first condition corresponds to the so-called "anti-aliasing" condition.

Furthermore, the judicious choice of the geometry of this spatial filtering device will make it possible to isolate, according to the invention, the useful signal from the various components of noise.

This filtering device is for example constituted by a rectangular diaphragm 2, positioned for example directly downstream of the object to be imaged OBJ, perpendicularly to the direction of observation (and hence almost parallel to the detection device), for example between the object to be imaged OBJ and the downstream plate of the sample holder, and elongated along a direction. This diaphragm 2 may for example consist of two slender plates of aluminum sheet 0.5 mm thick separated by around Y=4 mm. The observable zone upstream is thus of quasi-rectangular shape of about X mm and Y mm along two directions perpendicular to the direction of observation. We may for example take z as direction of observation, and x and y as axes for the diaphragm.

In the embodiment of the spatial filtering device COL represented in FIG. 5, this device COL furthermore comprises a lens 3 placed between the tank 1 and the detection device DET. The object focus of the lens 3 is situated in the plane of the diaphragm (possibly taking account of the optical index of the liquid serving for the acoustic coupling of the vibrations generating device TRANS, if the scattered signal wave DIF passes through this liquid). In the embodiment presented, a lens of focal length L=250 mm is used but other focal lengths may be suitable.

This spatial filtering device reduces the angular extent of the part SIG of the scattered signal wave DIF which reaches the detection device DET, this possibly being useful for adapting the size of the speckle grains to the dimension of the pixels of the camera.

Specifically, in the absence of any spatial filtering device, the signal wave DIF scattered by the object to be imaged OBJ may occupy a wide solid angle, of the order of Π steradians, and may be decomposed into a superposition of elementary plane waves with very different wave vectors $K_s$. Each wave vector $K_s$ has, in the plane of the detector $(x_D, y_D)$, two coordinates $K_x$ and $K_y$. To obtain utilizable information, it is necessary for the density of the fringes corresponding to the spatial modulation of the signal of interference of the scattered signal wave with the reference wave not to exceed the resolution of the matrix detector consisting of elementary detectors (so-called "anti-aliasing" condition). In particular, for a plane reference wave REF, with wave vector $K_0$, with coordinates in the plane of the detector $K_{x0}$, $K_{y0}$, this condition of density of the fringes gives rise to the "anti-aliasing" condition defined by:

$SK0 = SINC (d_x \cdot (K_x - K_{x0})) \cdot SINC (d_y \cdot (K_y - K_{y0})) \approx 1 - Ea$ where the function SINC of a dummy variable xx is defined as being equal to 1 for xx=0 and to sin xx/xx otherwise, where Ea is a decay factor quantifying the loss of contrast of the fringes that is related to the spatial integration of the detector, and where $d_x$ and $d_y$ represent respectively the characteristic dimensions of the elementary detectors of the detection device along the directions $x_D$ and $y_D$. Thus, the measurement must be limited to an elementary angular field of the signal wave SIG, corresponding to a cone of angle $(\pm \alpha_x; \pm \alpha_y)$ around the direction of the wave vector $K_o$ of the reference wave REF, the dimensions $\alpha_x$ and $\alpha_y$ of this elementary angular field having to be substantially less than or equal to $\lambda/2d_x$ and $\lambda/2d_y$ respectively so as to comply with said "anti-aliasing" condition, where $\lambda$ is the reference wavelength REF.

The use of the diaphragm downstream of the object to be imaged OBJ, makes it possible among other things to eliminate the components of the signal wave not complying with this "anti-aliasing" condition.

A judicious choice of the geometry of the spatial filtering device COL, and of the detection device makes it possible furthermore to isolate the useful signal from the various terms which appear in the signal resulting among other things from the analysis of the interferograms $I(U, V, W, r, t)$. The matter is discussed in the case of 4-phase demodulation but a similar discussion could be had in the case of detection by "frequency chirping", or other similar technique.

The interferogram $I(U, V, W, r, t)$ corresponds to the total intensity $I_T$ seen by the detection device, i.e. to the square of the modulus of the complex amplitude E $(I_T = |E|^2 = E \cdot E^*$ where $E^*$ is the complex conjugate of E). To simplify the discussion we shall consider only a single acoustic component of frequency $f_{AO} = f_I + H \cdot f_A$ (with H=1). The complex amplitude E results from the sum of the amplitude $E_R$ of the reference wave REF, of the amplitude $E_I$ of the part of the scattered signal wave SIG at the frequency of the incident wave $f_I$, and of the amplitude $E_S$ of the acoustic component of the signal wave of frequency $f_{AO}$. We therefore have $E = E_I + E_R + E_S$.

The total intensity $I_T$, which is used to extract the information item sought corresponds to the sum of 6 terms $(I = E \cdot E^* = (E_I + E_R + E_S) \cdot (E_I + E_R + E_S)^*)$:

the term $E_I \cdot E_I^*$ corresponds to the interference between the part of the signal wave scattered at the frequency $f_I$ and itself, that is to say to the interference between the ordinary speckle and the ordinary speckle, the term $E_S \cdot E_S^*$ corresponds to the interference between the acoustic component of the signal wave scattered at the acousto-optical frequency $f_{AO} = f_I + f_A$ and itself, that is to say to the interference between the acousto-optical speckle and the acousto-optical speckle, the term $E_R \cdot E_R^*$ corresponds to the interference between the reference wave and itself, the term $E_R \cdot E_I^*$ corresponds to the interference between the reference wave and the ordinary speckle, the term $E_I.E_S^*$ corresponds to the interference between the ordinary speckle and the acousto-optical speckle, and the term $E_R.E_S^*$ corresponds to the interference between the reference wave and the acousto-optical speckle, which constitutes the term carrying the relevant information.

The spatial filtering device COL makes it possible to reduce the angular extent of the wave emanating from the object which may behave at the level of the detection device as a quasi-plane wave. Such is the case in particular for the parts of the scattered signal wave having complex amplitude $E_I$ and $E_S$. Additionally, the reference wave REF is, in the present embodiment, a plane wave. On account of the spatial filtering device the 3 diagonal terms $E_R.E_R^*$, $E_I.E_I^*$ and $E_S.E_S^*$ (as well as the term $E_I.E_S^*$) vary slowly in space along the directions x and y of the detection device. Additionally the term $E_R.E_I^*$ varies rapidly in time (at a frequency of around approximately $f_A$) and is averaged to zero on account of the low acquisition frequency of the detector. The relevant term $E_R.E_S^*$ is therefore easy to isolate by suitable digital processing (this making it possible to determine $E_S$). If we choose a sufficient angular shift $\theta_Y$ between the reference wave and the scattered signal wave, this term is the only one to vary slowly over time, and rapidly in space along the Y direction. This Y direction corresponds to the direction of the width of the diaphragm, and to the direction $Y_D$ of the plane of the detector.

One way of extracting the relevant information consists in performing a Fourier transformation of the complex amplitude $E_S(U, V, W, r)$ calculated above, along the x and y directions of the plane of the detector (or possibly the direction y only). We then obtain a signal TF $E_s (U,V,W,k)$, k being the coordinate in the space of wave vectors. A mapping of the signal TF $E_S (U, V, W, k)$ obtained after Fourier transform is represented in FIG. 6, which is an angular representation in the space of wave vectors. The various terms contributing to the interferogram represented therein are discussed hereinafter.

The N-phase demodulation (or the "frequency chirping") should in theory make it possible to completely eliminate the term for the interference between the reference wave and the reference wave ($E_R.E_R^*$), if the experiment were perfectly stable over time. This is never perfectly the case, and a fairly significant nuisance component therefore remains. However, this term varies slowly along the x and y directions of the plane of the detector, thus leading, in the space of wave vectors, on account of the bidimensional Fourier transform, to a narrow peak centered on the origin of coordinates (zone 4 of FIG. 6).

The N-phase demodulation (or the "frequency chirping") should make it possible to eliminate the term for the interference between the ordinary speckle and the ordinary speckle ($E_I.E_I^*$), if the experiment were perfectly stable over time, and if the speckle remained static and did not self decorrelate. This is never perfectly the case, and a fairly significant nuisance component therefore remains (zone 2 of FIG. 6). This term is even the dominant noise term for certain objects to be imaged in which the speckle does not remain static, (for example for certain biological tissues). This term for the interference between the ordinary speckle and the ordinary speckle is, just like the term for the interference between the reference wave and the reference wave, centered on the origin of the space of wave vectors. On account of the use of the spatial filtering device defined previously, the amplitude of the ordinary speckle field has a finite angular extent, which corresponds to the interval [$-Y/2L; Y/2L$]. As the term for the interference between the ordinary speckle and the ordinary speckle corresponds to the intensity of the field, that is to say to the product of the complex amplitude and the conjugate complex amplitude, it is necessary, in order to evaluate its extent in the space of wave vectors, to convolve the speckle field with itself in the space of wave vectors. This interference term therefore has an angular extent that is twice as wide as the field itself (interval $[-Y_2=-Y/L; Y_2=+Y/L]$. Likewise, heightwise in the space of wave vectors, this term corresponds to the interval $[-X_2=-X/L; X_2=+X/L]$, if the latter satisfies the aliasing condition in the optimum case ($X/L=\lambda/2d_x$). This noise thus exhibits a delimited pyramidal shaped envelope which is centered on the origin of the coordinates of the space of wave vectors.

The interference between the acousto-optical speckle and the acousto-optical speckle ($E_S.E_S^*$) is a second order diagonal term. Apart from its lower intensity, this term is no different from the term for the interference between the ordinary speckle and the ordinary speckle described above.

The reference wave REF being at the frequency $f_R$ and the ordinary speckle being at the frequency $f_I$, the term for the interference between the reference wave and the ordinary speckle ($E_R.E_I^*$) is at a frequency of about $f_R-f_I$ about equal to $f_A$ i.e. about 2.2 MHz. This interference term is thus averaged to zero over the duration of acquisition of each image on account of the low acquisition frequency of the detection device and may therefore be neglected.

Likewise, the term for the interference between the ordinary speckle and the acousto-optical speckle ($E_I.E_S^*$), in addition to being a second order term, also possesses a frequency about equal to the frequency of the acoustic wave $f_A$ and may therefore be averaged to zero over the duration of acquisition of each image. It may therefore be neglected.

The relevant term to be extracted from the interference between the signal wave SIG and the reference wave REF is therefore the term for the interference between the reference wave and the acousto-optical speckle ($E_R.E_S^*$). This term corresponds to zone 3 and to the interval $[Y_{3-}; Y_{3+}]$ of FIG. 6. As this term corresponds to the interference of a speckle emanating from the diaphragm 2 and of a plane wave, the interval $[Y_{3-}; Y_{3+}]$ has the same angular width as the angle of view of the diaphragm i.e. $Y_{3-}-Y_{3+}=Y/L$. This term evolves over time at the detection frequency $f_R-f_{AO}$ (=$f_c/4$ in the case of 4-phase demodulation, and =0 in the case of "frequency chirping"). It may therefore be measured by the electronic detection device. Additionally, as the reference wave is shifted angularly, the center of the zone 3 is shifted angularly by $\theta_Y$ (where the angle $\theta_Y$ is, as defined previously, the angle between the reference wave REF and the signal wave SIG). The choice of the angle $\theta_Y$ defines the position of the center of zone 3, which is anyway of extent Y/L, when using a diaphragm of width Y. It is therefore appropriate to devise matters in such a way that zones 2 and 3 do not overlap so as to obtain, on the pixels of zone 3, useful information only.

For example, we can choose $\theta_Y=3Y/2L$, this giving $Y_{3+}=2Y/L$, and $Y_{3-}=Y/L=Y_2$. Thus, the outer edge of zone 2 and the inner edge of zone 3 are superimposed without the two zones overlapping. Neither is there then any blank part between zones 2 and 3 of FIG. 6. The signal of interference of the reference wave with the acousto-optical speckle has thus been separated in the space of wave vectors from the terms of the intensity of the reference and of the intensity of the speckle, which are situated at the center (zones 4 and 2 of FIG. 6) of the space of wave vectors.

The extent of zone 3 being directly proportional to Y, there will be a temptation to increase the width of the diaphragm so long as the "aliasing" condition $Y_{3+}<\lambda/2d_Y$ is complied with.

There is however a compromise to be made between on the one hand maximizing the area of zone 3 by increasing the width Y of the diaphragm, and on the other hand maximizing the integral of the product between area and effectiveness over this zone. This effectiveness corresponds to the loss of contrast of the interferograms on account of the integration of the interferograms over pixels of finite size. For adjoining pixels, an effectiveness factor is found according to a sinc law similar to that introduced previously for the "aliasing". In this case, the effectiveness vanishes when the angle of "aliasing" $\lambda/2d_Y$ is reached. For example, $Y_{3+}$ may be chosen to be appreciably less than the limit of "aliasing", for example $Y_{3+}=(2/3).\lambda/2d_Y$ approximately, so as to leave about a sixth of the area of the detection device inactive on each side, so that the effectiveness is sufficient. $Y_{3+}$ being equal to $2Y/L$, this makes it possible to adapt, as a function of the laser used and of the detector used, the characteristics of the spatial filtering device.

FIG. 6 thus represents the mapping of the zones obtained in the space of wave vectors by the present invention after the bidimensional Fourier transform. This map may be decomposed into a central column or zone 2, of extent $[-Y/L, Y/L]$, a left column or zone 1, and a right column or zone 3. Inside zone 2, zone 4 represents the term for the interference between the wave of the reference and itself ($E_R.E_R^*$). To first order, if there is no acoustic signal, the noise observed on the image outside of zones 2 and 4 corresponds to the "shot-noise" associated with the reference wave. In the presence of an acoustic signal, zone 3 represents the region of the space of wave vectors wherein is detected the useful signal according to the invention. According to the sign of the angle of incidence $\theta_Y$, zone 3 could of course be situated on the left of FIG. 6.

The relevant information, which makes it possible to calculate the complex amplitude $E_S$ of the acoustic component, corresponds to the interference between the reference wave and the acousto-optical speckle ($E_R.E_S^*$). A digital information item relating to the measurement point (U, V, W) of the object to be imaged is for example obtained by summing the intensities calculated over the pixels of zone 3 ($|TF\ E_S|^2$). The sum of the intensities of the pixels of zone 1 symmetric with zone 3 with respect to the vertical axis of FIG. 6 may serve as control. It is also possible to subtract from the sum of the intensities of the pixels of zone 3 the sum of the intensities of the pixels of zone 1, thereby making it possible to reduce any systematic measurement errors. The sum of the intensities measured over zone 2 also carries information, since it characterizes the level of noise associated with the decorrelation of the speckle.

It is also possible to use conventional means of image processing, to average, after 4-phase demodulation, Fourier transform and calculation of the intensity, the intensities of the pixels for example 8 by 8, 16 by 16, or 32 by 32, so as to display a control mapping of the signal obtained for the measurement point, with coordinates (U, V, W) (to verify for example the positioning of the various zones).

We may also only carry out for each row of the detection device, a unidimensional Fourier transform (along y for the examples considered), in which case the signal $TF_1\ E_S\ (U, V, W, k)$ is not exactly the one represented in FIG. 6, but zone 4 extends over the entire X-Y extent of this figure. The remainder of the processing remains valid.

We thus obtain the sought-after digital information item, relating to the measurement point, with coordinates (U, V, W) of the object to be imaged OBJ, in the case of 4-phase demodulation. For "frequency chirping", or the like, the digital information item thus obtained relates to the acoustic frequency $f_A$ used, and we obtain the coordinates and the digital information relating to various points of the interval $[U-Dx; U+Dx]$ by the means described above.

The choice of the angle $\theta_Y$ makes it possible to properly separate the signals obtained, but the appropriate positioning of the device making it possible to use a given angle $\theta_Y$ may require a control step. In this control step we obtain an image, for example by suppressing the acoustic wave and adjusting the frequency $f_R$ of the reference wave, so as to detect the component of the scattered field at the frequency $f_I$. We choose for example $f_R=f_I+f_c/4$ and we perform a 4-phase demodulation. The lens is positioned precisely in such a way that a sharp image of the zone seen through the diaphragm 4 is obtained by Fourier transform of the signal detected in the plane of the detection device.

As seen previously, in a Fourier transform calculation, the edge of the calculation matrix corresponds to the "aliasing" condition. The control step makes it possible to ensure, for example, that the outer edge of the zone containing the useful signal is not too close to the edge of the calculation matrix, and/or that the zone containing noise and the zone containing the useful signal are in contact at the level of the inner edge of this zone, but do not overlap.

FIG. 7 represents a second exemplary implementation of the method according to the invention in which the spatial filtering device is not used. Specifically, for low laser intensities, and if the speckle decorrelation term is not too large, the "shot-noise" becomes the dominant noise. Such is the case when with the first exemplary implementation (FIG. 5), the values of the sums, measured over zones 1 and 2, are about the same. This configuration is also useful for other applications where the acoustic wave is of sufficient power to reach a sufficient acousto-optical conversion yield. The signal associated with the acoustic component may then be larger than the speckle decorrelation noise.

It is possible to dispense with the spatial filtering device since, even if the term for the interference between the ordinary speckle and the ordinary speckle ($E_I.E_I^*$) can then no longer be separated spatially from the relevant term ($E_R.E_S^*$), it remains very much less than the "shot-noise" of the reference wave. It is also possible in this case to choose a zero angle $\theta_Y$, for example with the aid of a semireflecting pane. Only the term for the interference between the reference wave and itself ($E_R.E_R^*$), which is highly centered on the few pixels of zone 4 of FIG. 6, constitutes a noise term to be filtered. This filtering is carried out simply by digitally eliminating the components of the space of wave vectors round about (0, 0), excluding zone 4 from the summation over the pixels of the intensities of the signal. It may even be that this noise term is negligible, and it is then possible to compute the sum of the intensities over the pixels in the real space rather than in the space of wave vectors (and it is no longer necessary in this case to perform a Fourier transformation).

Figure 8:
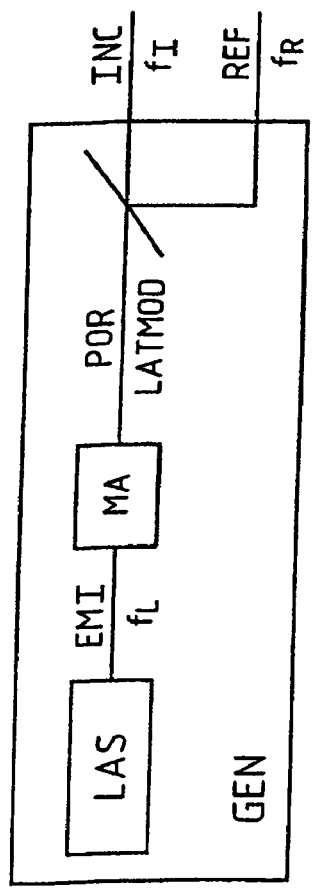
FIG. 8 is a detailed diagram of another example of the device for generating two coherent waves according to the present invention.

FIG. 8 represents another generating device used to implement the method according to the invention in the particular case of the second example of FIG. 7. The emission wave EMI, of wavelength $\lambda$, emitted by the laser LAS, is intercepted by an amplitude modulation device MA. This device generates a carrier wave POR, of frequency $f_I$, and two amplitude-modulated lateral bands LATMOD and LATMOD', of frequency $f_R$. These three waves are applied to a semitransparent pane, which transmits a part of each of these waves applied to the object to be imaged OBJ. The transmitted part of the carrier wave constitutes the incident wave INC. Furthermore, the semitransparent pane reflects a part of each of these waves towards the detection device, the reflected part of LATMOD constituting the reference wave REF.

This device is only adapted to the second embodiment, where no spatial filtering device is used, since in the case of an intensity modulation lateral band, the spatial filtering does not make it possible to separate the various interference terms.

Figure 9:
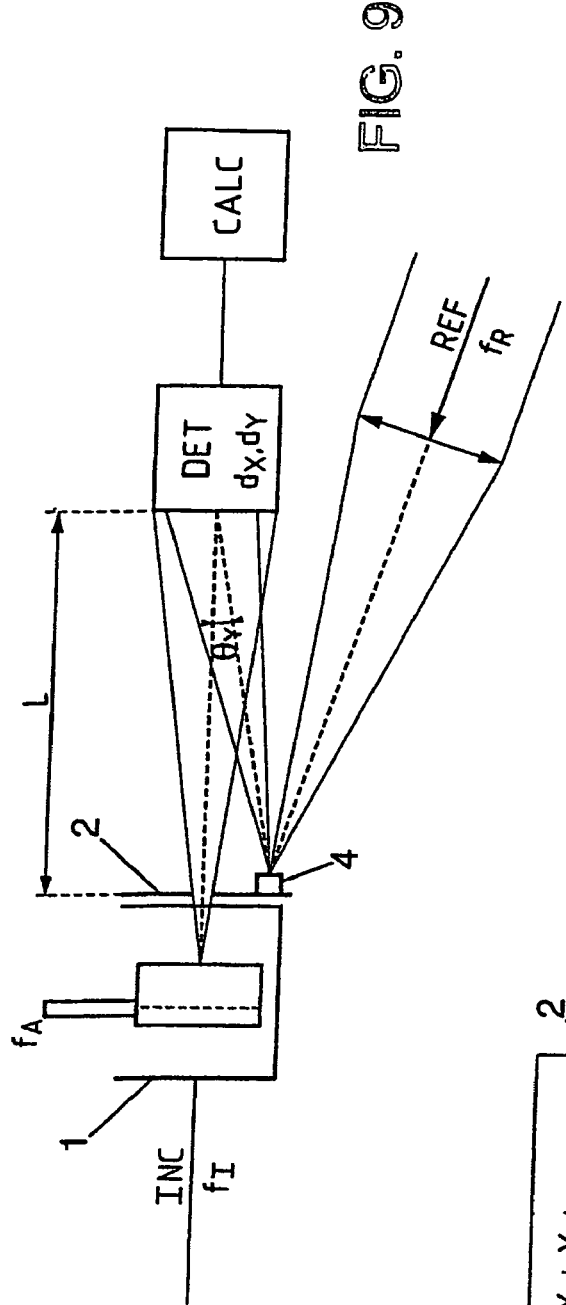
FIG. 9 represents a detail of a third embodiment of the invention.

FIG. 9 describes a detail of a third embodiment of the present invention and of the spatial filtering device. Numerous characteristics have already been described when presenting the first embodiment, and will therefore not be described again. In this third embodiment, the reference wave REF is no longer a plane wave, but a spherical wave of frequency $f_R$. Such a spherical reference wave may for example be obtained, on the basis of the plane reference wave generated by a generating device GEN described previously, by focusing the plane reference wave, with the aid of a lens 5, onto a small mirror 4 situated for example in the plane of the diaphragm 2. The reference wave REF may moreover arrive on the mirror 4 at an angle $\theta_Y$ so that it is reflected and arrives at the detection device DET while forming an angle $\theta_Y$ with the signal wave SIG. In this embodiment, one does not necessarily use a convergent lens 3 to collimate the signal wave heading for the detector DET, specifically, the divergent nature of the reference wave fulfils a similar role.

Furthermore, the diaphragm 2 can be taken out of the sample holder of the object to be imaged OBJ, and can be placed between the tank and the detection device DET, or possibly can be fixed onto the front face of the tank 1. This provision may be beneficial if the acoustic coupling between the transducer TRANS, of acoustic frequency $f_A$, and the object to be imaged OBJ is effected by a tank filled with water 1, and when the latter is situated on the light path travelled by the reference wave REF before reaching the mirror 4. (This provision is also valid for the other embodiments where a diaphragm is used).

The processing of the interferograms measured is then identical to the processing setforth previously, where L now represents the distance between the diaphragm 2 and the detection device DET.

Figure 10:
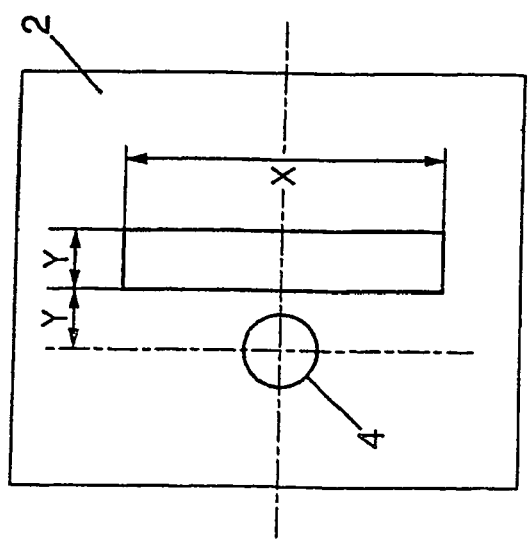
FIG. 10 represents the rear face of the diaphragm used in the third embodiment.

FIG. 10 represents the diaphragm 2 furnished with the mirror 4, visualized from the detection device DET. The diaphragm 2 exhibits a slit, for example central, of width Y and of height X. To obtain an image such as represented in FIG. 6, a mirror 4, for example circular, is placed midway up the height of the slit. The mirror 4 is moreover shifted laterally with respect to the slit of the diaphragm 2. This lateral shift is related to the shift of zones 2 and 3 of FIG. 6 that one seeks to effect, once the calculations have been performed by the processing device CALC. By choosing for example an angular lateral offset equal to $\theta_Y$ between the source point of the reflected reference wave and the edge closest to the mirror of the slit of the diaphragm 2, seen from the detection device, we obtain zones 2 and 3 of FIG. 6 juxtaposed but not superimposed. In this case, care will of course be taken to choose a mirror 4 of dimensions such that the mirror does not encroach on the slit of the diaphragm 2. Thus, it is easy to separate zones 2 and 3 of FIG. 6.

This embodiment makes it possible moreover to easily find an optimal position of the detector DET making it possible to obtain information of good quality for the point studied (U, V, W) of the object to be imaged OBJ. Specifically, by increasing L, that is to say by distancing the detection device DET from the diaphragm 2, the angle between the signal wave SIG and the reference wave REF decreases, so that the "aliasing" condition is better complied with. On the other hand, the intensity of the signal decreases with this distance. L. The compromise to be made between the effectiveness of detection and the size of the zone 3 of FIG. 6, already mentioned, is effected simply by the positioning of the detection device DET with respect to the diaphragm 2.

In this embodiment, the optimal positioning of the detector is carried out independently of the relative positioning of zones 2 and 3 of FIG. 6, which, itself, is carried out by the appropriate placing of the point of focusing of the reference wave (center of the mirror 4 on the diaphragm 2).

By implementing the method described previously, according to any one of its embodiments represented in FIGS. 1 to 10, we have obtained digital information relating to the measurement point, with coordinates (U, V, W) of the object (in the case of N-phase demodulation) or relating to each point of the interval ([U−Dx,U+Dx], V, W) of the points of the object (in the case of "frequency chirping" or other similar procedure), that is to say pointwise or 1D information.

To obtain an image of the 2D or 3D object, it is required to repeat the whole set of operations described above after having displaced the position of the focal point of the acoustic wave along the other directions (x or y or z for the N-phase demodulation) (y or z for the "frequency chirping"). The displacement of the position of the focal point may be achieved, either by displacing the transducer (along the direction x, y or z considered) while preserving the acoustic coupling between the transducer and the object to be imaged, or by using several transducers with different focal points, for example.

It may be beneficial to displace the spatial filtering device COL (if one is being used), the detector DET, or even the device used to make the reference wave interfere on the detector, and all or part of the generating device GEN conjointly with the displacement of the position of the focal point i.e. of the point of measurement with coordinates (U, V, W). Alternatively, it may possibly be preferable to displace only the object to be imaged in the opposite direction so as not to have to perform a similar movement on the whole of the remainder of the installation.

As an acoustic transducer is used, any device according to the invention may furthermore be coupled to a conventional acoustic imaging device. The coupling of these two devices thus makes it possible to obtain from the object to be imaged OBJ purely acoustic information provided by the acoustic transducer by a conventional technique of ultrasound imaging, and optical information provided by the device according to the invention.

The invention claimed is:

1. A method of acousto-optical imaging of an object to be imaged comprising the steps:
   (a) generating an incident optical wave, of frequency $f_I$, and a reference optical wave, of frequency $f_R$, this reference wave being coherent with the incident wave, and exhibiting therewith a known phase difference $\phi_i(t)$,
   (b) vibrating in a first object direction and at an acoustic frequency $f_A$, a zone of the object to be imaged with the aid of a vibration generating device, and generating an acoustic wave, focused at a focal point situated in the object to be imaged,
   (c) applying said incident wave to the object to be imaged, and thus generating a scattered signal wave,
   (d) applying at least a part of the scattered signal wave to a detection device,
   (e) applying the reference wave to the detection device without making it pass through the object to be imaged, thereby generating at the point r of the detection device an interferogram I(r, t) varying over time t,
   (f) extracting a digital information item from the interferogram I(r, t),
   (g) obtaining the coordinates of the focal point of the object to be imaged, to which the digital information item relates, and
   (e) repeating steps (a) to (g) for various focal points of the acoustic wave in the object to be imaged, these various focal points being aligned along the first object direction.

2. The method of acousto-optical imaging as claimed in claim 1, in which in the course of step (f), an acoustic component of the part of the scattered signal wave applied to the detection device is detected, this acoustic component being at a frequency corresponding to the sum of the frequency $f_I$ of the incident wave and of a harmonic of the acoustic frequency $f_A$.

3. The method of acousto-optical imaging as claimed in claim 2, in which, in the course of step (a), said reference wave is generated at a frequency $f_R$ equal or substantially equal to the sum of the frequency $f_I$ of the incident wave and of said harmonic of the acoustic frequency $f_A$.

4. A method of acousto-optical imaging of an object to be imaged comprising the steps:
  (a) generating an incident optical wave, of frequency $f_I$, and a reference optical wave, of frequency $f_R$, this reference wave being coherent with the incident wave, and exhibiting therewith a known phase difference $\phi_i(t)$,
  (b) vibrating in a first object direction and at acoustic frequency $f_A$, a zone of the object to be imaged with the aid of a vibration generating device,
  (c) applying said incident wave to the object to be imaged, and thus generating a scattered signal wave,
  (d) applying at least a part of the scattered signal wave to a detection device,
  (e) applying the reference wave to the detection device without making it pass through the object to be imaged, thereby generating at the point r of the detection device an interferogram I(r, t) varying over time t,
  (f) extracting a digital information item from the interferogram I(r, t), and
  (g) obtaining the coordinates of a point of measurement of the object to be imaged, to which the digital information item relates,
  in which, in the course of a first iteration, steps (a) to (f) are performed for a first frequency $f_A$ of the acoustic wave and a first frequency $f_R$ of the reference wave, in the course of at least a second iteration, steps (a) to (f) are repeated for a second frequency $f'_A$ of the acoustic wave and a second frequency $f'_R$ of the reference wave, these second frequencies being coded respectively with the first frequencies, the method furthermore comprising a step in the course of which:
  (f') at least one digital information item is obtained by decoding said digital information items obtained in the course of steps (f) of each iteration as a function of the frequencies used, and
  in which, in the course of step (g), the coordinates of at least one point of measurement of the object to be imaged to which the digital information item obtained in the course of step (f') relates are obtained, by decoding the said digital information items obtained in the course of steps (f) of each iteration as a function of the frequencies used.

5. The method as claimed in claim 4, in which the sequence of following operations is performed:
  a scan is performed of the frequency of the acoustic wave, which is focused on an interval of points with coordinates extending around the point with coordinates along the first object direction,
  a scan is performed jointly of the frequency $f_R$ of the reference wave in such a way as to keep $f_R$ substantially equal or equal to $f_I \pm H.f_A$, H being a nonzero integer,
  an interferogram $I(f_A, V, W, r)$ associated with the set of points of the extended interval is recorded for each pixel r and for each frequency $f_A$;
  a 1D frequency-time Fourier transformation is performed, for each pixel r, according to the frequency $f_A$ of the interferogram $I(f_A, V, W, r)$, and at least one interferogram I(r) associated at least with a measurement point with coordinates is obtained by replacing the time obtained after the Fourier transform with the magnitude U' along the first object direction $(x_o)$ with the aid of the speed of propagation of the acoustic wave in the object to be imaged.

6. The method of acousto-optical imaging as claimed in claim 1, in which at least steps (a) to (g) are repeated after having imposed a displacement of the vibration generating device relative to the object to be imaged along a direction not parallel to the first object direction $(x_o)$ of the object to be imaged.

7. A method of acousto-optical imaging of an object to be imaged comprising the steps:
  (a) generating an incident optical wave, of frequency $f_I$, and a reference optical wave, of frequency $f_R$, this reference wave being coherent with the incident wave, and exhibiting therewith a known phase difference $\phi_i(t)$,
  (b) vibrating in a first object direction and at an acoustic frequency $f_A$, a zone of the object to be imaged with the aid of a vibration generating device,
  (c) applying said incident wave to the object to be imaged, and thus generating a scattered signal wave,
  (d) applying at least a part of the scattered signal wave to a detection device,
  (e) applying the reference wave to the detection device without making it pass through the object to be imaged, thereby generating at the point r of the detection device an interferogram I(r, t) varying over time t,
  (f) extracting a digital information item from the interferogram I(r, t), and estimating the complex amplitude $E_s(r)$ of the acoustic component on the basis of the interferogram I(r,t), and
  (g) obtaining the coordinates of a point of measurement of the object to be imaged, to which the digital information item relates.

8. The method of acousto-optical imaging as claimed in claim 7, in which the detection device used is a monopixel detector, and in which, in the course of step (f), the digital information item is obtained as being the intensity of the field of complex amplitude $E_s(r)$ scattered by the object.

9. The method of acousto-optical imaging as claimed in claim 7, in which the detection device used is a multipixel detector, and in which in the course of step (f), the digital information is extracted as being the sum over at least a part of the pixels r of the detection device of the intensity of the complex amplitude field $E_s(r)$ scattered by the object.

10. The method of acousto-optical imaging as claimed in claim 7, in which, in the course of step (d) a spatial filtering device is used, in such a way as to limit, along at least one direction, the angular extent of the part of the scattered signal wave which is seen by each pixel of the detection device.

11. The method of acousto-optical imaging as claimed in claim 10, in which a spatial filtering device comprising a diaphragm, of dimensions X along a first diaphragm direction and Y along a third diaphragm direction, and a lens of focal length L with object focus situated directly downstream of the object to be imaged is used so as to limit the angular extent of the part of the scattered signal wave which is seen by each pixel of the detection device, and in which the reference wave applied to the detection device is globally a plane wave.

12. The method of acousto-optical imaging as claimed in claim 10, in which is used a spatial filtering device comprising a diaphragm of dimensions X along the first diaphragm direction and Y along the third diaphragm direction, disposed between the object to be imaged and the detection device at a distance L from the latter, so as to limit the angular extent of the part of the scattered signal wave which is seen by each pixel of the detection device, and in which the reference wave applied to the detection device is a spherical wave emanating from a source point situated in the plane of the diaphragm.

13. The method of acousto-optical imaging as claimed in claim 10, in which the reference wave and the scattered signal wave interfere on the detection device while forming a non-zero angle $\theta_Y$, $\theta_Y$ being measured in the plane of incidence of these two waves on the detection device.

14. The method of acousto-optical imaging as claimed in claim 10, in which the detection device used is a multipixel detector, and in which the part of the acoustic component, of complex amplitude $E_s(r)$, which varies rapidly in space in the plane of the detection device is isolated.

15. The method of acousto-optical imaging as claimed in claim 10, in which the detection device comprises pixels disposed as a matrix comprising rows along a first detector direction and columns along a third detector direction, and in which step (f) comprises the following steps:
   (f1) for at least one row or column a 1D-Fourier transform is done along this row or column of the detection device to the space of wave vectors, of the complex amplitude of the field $E_s(r)$, and a field $TF_1\ E_s(k)$, is thus obtained for this row or column,
   (f2) several zones of summation are defined in the space of wave vectors,
   (f3) the intensities of the field $TF_1\ E_s(k)$ at each point k of at least one zone are summed in this zone, and
   (f4) the digital information item is extracted as being a linear combination of the sums thus obtained at each zone.

16. The method of acousto-optical imaging as claimed in claim 10, in which the detection device comprises pixels disposed in a matrix comprising rows along a first detector direction and columns along a third detector direction, and in which step (f) comprises the following steps:
   (f1) a 2D-Fourier transform is done of the complex amplitude $E_s(r)$, from the plane of the detection device to the space of wave vectors, and a field $TF_2\ E_s(k)$, is thus obtained,
   (f2) several zones of summation are defined in the space of wave vectors,
   (f3) the intensities of the field $TF_2\ E_s(k)$ at each point k of at least one zone are summed in this zone, and
   (f4) the digital information item is extracted as being a linear combination of the sums thus obtained at each zone.

17. The method of acousto-optical imaging as claimed in claim 13, in which the angle $\theta_Y$ is about equal to 3Y/2L, in which, in the course of step (f2) are defined a first zone of summation, the so-called central zone, a second zone of summation, the so-called left zone, and a third zone of summation the so-called right zone, and in which, in the course of step (f4), the digital information item is extracted as being a linear combination of the value of the sum of the left zone and of the sum of the right zone.

18. A method of acousto-optical imaging of an object to be imaged comprising the steps:
   (a) generating an incident optical wave, of frequency $f_I$, and a reference optical wave, of frequency $f_R$, this reference wave being coherent with the incident wave and exhibiting therewith a known phase difference $\phi_i(t)$,
   (b) vibrating in a first object direction and at an acoustic frequency $f_A$, a zone of the object to be imaged with the aid of a vibration generating device,
   (c) applying said incident wave to the object to be imaged, and thus generating a scattered signal wave,
   (d) applying at least a part of the scattered signal wave to a detection device,
   (e) applying the reference wave to the detection device without making it pass through the object to be imaged, thereby generating at the point r of the detection device an interferogram I(r, t) varying over time t,
   (f) extracting a digital information item from the interferogram I(r, t), and
   (g) obtaining the coordinates of a point of measurement of the object to be imaged, to which the digital information item relates,
   wherein in the course of step (a),
   a laser source of wavelength $\lambda$ emits an emission wave, of frequency $f_L$,
   amplitude modulation means of the emission wave, generate a carrier wave of incident frequency $f_I$, and at least one amplitude modulation lateral band, which corresponds to a wave of frequency $f_R$,
   a semireflecting mirror, transmits a part of the lateral band wave and a part of the carrier wave forming the incident wave, and reflects a part of the carrier wave and a part of the lateral band wave forming the reference wave.

19. A method of acousto-optical imaging of an object to be imaged comprising the steps:
   (a) generating an incident optical wave, of frequency $f_I$, and a reference optical wave, of frequency $f_R$, this reference wave being coherent with the incident wave, and exhibiting therewith a known phase difference $\phi_i(t)$,
   (b) vibrating in a first object direction and at an acoustic frequency $f_A$, a zone of the object to be imaged with the aid of a vibration generating device,
   (c) applying said incident wave to the object to be imaged, and thus generating a scattered signal wave,
   (d) applying at least a part of the scattered signal wave to a detection device,
   (e) applying the reference wave to the detection device without making it pass through the object to be imaged, thereby generating at the point r of the detection device an interferogram I(r, t) varying over time t,
   (f) extracting a digital information item from the interferogram I(r, t), and
   (g) obtaining the coordinates of a point of measurement of the object to be imaged, to which the digital information item relates,
   wherein in the course of step (a),
   a laser source of wavelength $\lambda$ emits an emission wave, of frequency $f_L$,
   a first acousto-optical modulator transmits a part of the emission wave to form the incident wave on the object to be imaged, and moreover generates a first frequency shifted wave, the frequency of which is shifted by a value $\delta f_1$, possibly negative, with respect to the emission wave, and
   a second acousto-optical modulator intercepts the first frequency shifted wave and generates a second frequency shifted wave, the frequency of which is shifted by a value $\delta f_2$, possibly negative, with respect to the shifted wave, the second frequency shifted wave forming the reference wave, the frequency of which is thus shifted in frequency with respect to the incident wave by a value $\delta f = \delta f_1 + \delta f_2$, thus determining a known phase difference $\phi_i(t)$ between these two waves.

20. A method of acousto-optical imaging of an object to be imaged comprising the steps:
   (a) generating an incident optical wave, of frequency $f_I$, and a reference optical wave, of frequency $f_R$, this reference wave being coherent with the incident wave, and exhibiting therewith a known phase difference $\phi_i(t)$,
   (b) vibrating in a first object direction and at an acoustic frequency $f_A$, a zone of the object to be imaged with the aid of a vibration generating device, (c) applying said incident wave to the object to be imaged, and thus generating a scattered signal wave, (d) applying at least a part of the scattered signal wave to a detection device, (e) applying the reference wave to the detection device without making it pass through the object to be imaged, thereby generating at the point r of the detection device an interferogram I(r, t) varying over time t, (f) extracting a digital information item from the interferogram I(r, t), and (g) obtaining the coordinates of a point of measurement of the object to be imaged, to which the digital information item relates, wherein in the course of step (a), two independent laser sources, locked in phase by electronic slaving, generate the incident and reference waves, exhibiting a known phase difference $\phi_i(t)$ between them.

21. A method of acousto-optical imaging of an object to be imaged comprising the steps:

(a) generating an incident optical wave, of frequency $f_I$, and a reference optical wave, of frequency $f_R$, this reference wave being coherent with the incident wave, and exhibiting therewith a known phase difference $\phi_i(t)$, (b) vibrating in a first object direction and at an acoustic frequency $f_A$, a zone of the object to be imaged with the aid of a vibration generating device, (c) applying said incident wave to the object to be imaged, and thus generating a scattered signal wave, (d) applying at least a part of the scattered signal wave to a detection device, (e) applying the reference wave to the detection device without making it pass through the object to be imaged, thereby generating at the point r of the detection device an interferogram I(r, t) varying over time t, (f) extracting a digital information item from the interferogram I(r, t), and (g) obtaining the coordinates of a point of measurement of the object to be imaged, to which the digital information item relates, wherein in the course of step (a), a laser source of wavelength λ emits an emission wave, of frequency $f_L$, a semireflecting mirror transmits a part of the emission wave to form the incident wave on the object to be imaged, and transmits a second part of the emission wave, a first acousto-optical modulator intercepts the second part of the emission wave and generates a first frequency shifted wave, with frequency shifted by a value $\delta f_1$, possibly negative, with respect to the emission wave, and a second acousto-optical modulator intercepts the first frequency shifted wave and generates a second frequency shifted wave, the frequency of which is shifted by a value $\delta f_2$, possibly negative, with respect to the shifted wave, the second frequency shifted wave forming the reference wave, the frequency of which is thus shifted in frequency with respect to the incident wave by a value $\delta f = \delta f_1 = \delta f_2$, thus determining a known phase difference $\phi_i(t)$ between these two waves.

22. The method of acousto-optical imaging as claimed in claim 1 in which the object to be imaged is a biological tissue.

23. A method of acousto-optical imaging of an object to be imaged comprising the steps:

(a) generating an incident optical wave, of frequency $f_I$, and a reference optical wave, of frequency $f_R$, this reference wave being coherent with the incident wave, and exhibiting therewith a known phase difference $\phi_i(t)$, (b) vibrating in a first object direction and at an acoustic frequency $f_A$, a zone of the object to be imaged with the aid of a vibration generating device, (c) applying said incident wave to the object to be imaged, and thus generating a scattered signal wave, (d) applying at least a part of the scattered signal wave to a detection device, (e) applying the reference wave to the detection device without making it pass through the object to be imaged, thereby generating at the point r of the detection device an interferogram I(r, t) varying over time t, (f) extracting a digital information item from the interferogram I(r, t), and (g) obtaining the coordinates of a point of measurement of the object to be imaged, to which the digital information item relates, wherein the vibration generating device is used to obtain an acoustic cue of the zone of the object to be imaged, and in which the digital information item extracted in step (f) is used jointly with said acoustic cue.

24. An installation for acousto-optical imaging of an object to be imaged comprising:

means for generating an incident optical wave, of frequency $f_I$, and a reference optical wave of frequency $f_R$, this reference wave being coherent with the incident wave and exhibiting therewith a known phase difference $\phi_i(t)$, a vibration generating device for vibrating in a first object direction and at an acoustic frequency $f_A$ a zone of the object to be imaged, means for applying the said incident wave to the object to be imaged, thus generating a scattered signal wave, a detection device, means for applying at least part of this scattered signal wave to the detection device, means for applying the reference wave to the detection device without making it pass through the object to be imaged, thereby generating at point r of the detection device an interferogram I(r, t) varying over time t, and means for extracting a digital information item, estimating the complex amplitude $E_s(r)$ of the acoustic component on the basis of the interferogram I(r,t), and obtaining the coordinates of a point of measurement of the object to be imaged, to which the digital information item relates, from the interferogram.

25. The installation for acousto-optical imaging as claimed in claim 24 furthermore comprising the following elements:

means for visualizing said digital information item relating to said point of measurement of the object to be imaged, and means for displacing the object to be imaged.

26. The installation for acousto-optical imaging as claimed in claim 24, furthermore comprising a spatial filtering device situated downstream of the object to be imaged.

27. The method of acousto-optical imaging as claimed in claim 4, in which at least steps (a) to (g) are repeated after having imposed a displacement of the vibration generating device relative to the object to be imaged along a direction not parallel to the first object direction ($x_o$) of the object to be imaged.

28. The method of acousto-optical imaging as claimed in claim 4 in which the object to be imaged is a biological tissue.

29. The method of acousto-optical imaging as claimed in claim 7 in which the object to be imaged is a biological tissue.

* * * * *

UNITED STATES PATENT AND TRADEMARK OFFICE
CERTIFICATE OF CORRECTION

PATENT NO.       : 7,623,285 B2                                          Page 1 of 1
APPLICATION NO.  : 10/549511
DATED            : November 24, 2009
INVENTOR(S)      : Michel Jean Gross It is certified that error appears in the above-identified patent and that said Letters Patent is hereby corrected as shown below:

In Column 18, line 64 delete "(e)" and insert -- (h) --

In Column 19, line 15 delete "freguency" and insert -- frequency --

In Column 19, line 19 delete "at" and insert -- at an --

In Column 21, line 59 delete "wave" and insert -- wave, --

In Column 23, line 16 delete "$\Phi_i(t)$" and insert -- $\Phi_i(t)$ --

In Column 23, line 55 delete "$\delta f_1 = \delta f_2$," and -- $\delta f_1 + \delta f_2$, --

Signed and Sealed this

Twenty-sixth Day of January, 2010

David J. Kappos
*Director of the United States Patent and Trademark Office*